United States Patent
Hamada et al.

(10) Patent No.: US 10,099,997 B2
(45) Date of Patent: Oct. 16, 2018

(54) ACRYLIC ACID DERIVATIVE-CONTAINING COMPOSITION, AND METHOD FOR STABILIZING ACRYLIC ACID DERIVATIVE

(71) Applicant: DAIKIN INDUSTRIES, LTD., Osaka (JP)

(72) Inventors: Tomohito Hamada, Osaka (JP); Yosuke Kishikawa, Osaka (JP); Makoto Matsuura, Osaka (JP); Asako Yoshiyama, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 15/564,926

(22) PCT Filed: Apr. 8, 2016

(86) PCT No.: PCT/JP2016/061626
§ 371 (c)(1),
(2) Date: Oct. 6, 2017

(87) PCT Pub. No.: WO2016/163553
PCT Pub. Date: Oct. 13, 2016

(65) Prior Publication Data
US 2018/0093940 A1 Apr. 5, 2018

(30) Foreign Application Priority Data
Apr. 9, 2015 (JP) .................. 2015-080383

(51) Int. Cl.
*C07C 69/653* (2006.01)
*C07C 67/62* (2006.01)
*C07C 31/02* (2006.01)

(52) U.S. Cl.
CPC ............ *C07C 69/653* (2013.01); *C07C 67/62* (2013.01); *C07C 31/02* (2013.01)

(58) Field of Classification Search
CPC .................................................. C07C 69/653
USPC ........................................................ 560/223
See application file for complete search history.

(56) References Cited

U.S. PATENT DOCUMENTS

2012/0059187 A1 3/2012 Ishii et al.
2012/0283468 A1 11/2012 Kreis et al.

FOREIGN PATENT DOCUMENTS

| JP | 56-122331 | 9/1981 | | |
|---|---|---|---|---|
| JP | 56122331 A | * | 9/1981 | |
| JP | 2-17151 | 1/1990 | | |
| JP | 0217151 A | * | 1/1990 | |
| JP | 2-193944 | 7/1990 | | |
| JP | 02193944 A | * | 7/1990 | |
| JP | 10-504553 | 5/1998 | | |
| JP | 10504553 A | * | 5/1998 | |
| JP | 2005-239564 | 9/2005 | | |
| JP | 2005239564 A | * | 9/2005 | ............ B01D 3/141 |
| JP | 2011-1340 | 1/2011 | | |
| JP | 2012-530756 | 12/2012 | | |
| WO | 96/06066 | 2/1996 | | |

OTHER PUBLICATIONS

International Search Report dated Jul. 12, 2016 in International (PCT) Application No. PCT/JP2016/061626.

* cited by examiner

*Primary Examiner* — Deborah D Carr
(74) *Attorney, Agent, or Firm* — Wenderoth, Lind & Ponack, L.L.P.

(57) ABSTRACT

An object of the present invention is to provide a method for stabilizing an acrylic acid derivative, and a composition containing an acrylic acid derivative in which the acrylic acid derivative is stabilized. The present invention provides a composition comprising: (A) an acrylic acid derivative represented by Formula (I):

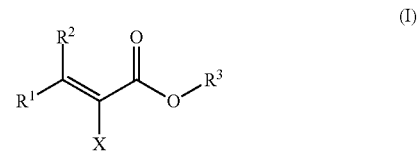

(wherein $R^1$ and $R^2$ are the same or different, and each represents alkyl, fluoroalkyl, aryl that may have one or more substituents, halogen, or hydrogen; $R^3$ represents alkyl, fluoroalkyl, aryl that may have one or more substituents, or hydrogen; and X represents fluoroalkyl, alkyl, halogen, or hydrogen); and (B) alcohol, wherein the content of acrylic acid derivative (A) is 30% (w/w) or more.

10 Claims, No Drawings

ACRYLIC ACID DERIVATIVE-CONTAINING COMPOSITION, AND METHOD FOR STABILIZING ACRYLIC ACID DERIVATIVE

TECHNICAL FIELD

The present invention relates to a composition containing an acrylic acid derivative, a method for stabilizing an acrylic acid derivative, and the like.

BACKGROUND ART

Acrylic acid derivatives are widely used for (1) materials of water-absorbing polymers, (2) materials of acrylic resins as a substitute for inorganic glass for use in window materials for buildings and vehicles, coverings for lighting equipment, lantern signs, road signs, daily necessities, office supplies, crafts, windscreens of watches, and the like, and (3) acrylic resin coating materials. Among acrylic acid derivatives, fluorine-containing acrylic acid derivatives are useful as synthetic intermediates of pharmaceuticals (e.g., antibiotics), synthetic intermediates for sheath materials of optical fibers, synthetic intermediates of coating materials, synthetic intermediates of semiconductor resist materials, and monomers of functional polymers.

Examples of known methods for producing an acrylic acid derivative include a method of producing an acrylic acid derivative by oxidizing isobutylene or propylene, and a method of producing an acrylic acid derivative using ethylene, propyne, or the like as a starting material using a transition metal catalyst.

Further, as examples of methods for producing a fluorine-containing acrylic acid derivative, for example, Patent Document 1 discloses a method of reacting a 2-fluoropropionic ester with a nitrogen-bromine-bond-containing brominating agent in the presence of a radical initiator, and Patent Document 2 discloses a process for converting a 3-halo-2-fluoropropionic acid derivative to a substituted 2-fluoroacrylic acid derivative in the presence of at least one kind of base and at least one kind of polymerization inhibitor.

CITATION LIST

Patent Documents

Patent Document 1: JP2011-001340A
Patent Document 2: JP2012-530756A

SUMMARY OF INVENTION

Technical Problem

Since an acrylic acid derivative contains an active unsaturated bond due to its structure, it is unstable against external stimuli such as heat, light, and oxygen, and may easily change into an oligomer or a polymer by a polymerization reaction or the like.

Therefore, a method for stabilizing an acrylic acid derivative, and a composition comprising an acrylic acid derivative in which the acrylic acid derivative is stabilized, have been in demand.

An object of the present invention is to provide a method for stabilizing an acrylic acid derivative, and a composition comprising an acrylic acid derivative in which the acrylic acid derivative is stabilized.

Solution to Problem

The inventors of the present invention conducted extensive research and found that the above problem can be solved by a composition comprising:

(A) an acrylic acid derivative represented by Formula (I):

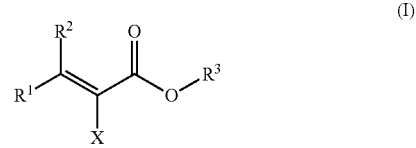

(wherein $R^1$ and $R^2$ are the same or different, and each represents alkyl, fluoroalkyl, aryl that may have one or more substituents, halogen, or hydrogen; $R^3$ represents alkyl, fluoroalkyl, aryl that may have one or more substituents, or hydrogen; and X represents fluoroalkyl, alkyl, halogen, or hydrogen); and (B) alcohol.

With this finding, the inventors completed the present invention.

The present invention includes the following aspects.

Item 1.

A composition comprising:

(A) an acrylic acid derivative represented by Formula (I):

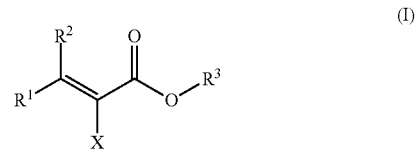

(wherein $R^1$ and $R^2$ are the same or different, and each represents alkyl, fluoroalkyl, aryl that may have one or more substituents, halogen, or hydrogen; $R^3$ represents alkyl, fluoroalkyl, aryl that may have one or more substituents, or hydrogen; and X represents fluoroalkyl, alkyl, halogen, or hydrogen); and (B) alcohol, wherein the content of acrylic acid derivative (A) is 30% (w/w) or more.

Item 2.

The composition according to Item 1, wherein alcohol (B) is $C_{1-6}$ alcohol.

Item 3.

The composition according to Item 2, wherein alcohol (B) is methanol.

Item 4.

The composition according to any one of Items 1 to 3, wherein $R^1$ is hydrogen, $C_{1-20}$ alkyl, or $C_{1-20}$ fluoroalkyl.

Item 5.

The composition according to any one of Items 1 to 4, wherein $R^1$ is hydrogen.

Item 6.

The composition according to any one of Items 1 to 5, wherein $R^2$ is hydrogen, $C_{1-20}$ alkyl, or $C_{1-20}$ fluoroalkyl.

Item 7.

The composition according to any one of Items 1 to 6, wherein $R^2$ is hydrogen.

Item 8.

The composition according to any one of Items 1 to 7, wherein $R^3$ is $C_{1-20}$ linear alkyl.

Item 9.

The composition according to any one of Items 1 to 8, wherein X is $C_{1-20}$ fluoroalkyl, fluorine, or chlorine.

Item 10.

The composition according to any one of Items 1 to 9, wherein X is fluorine.

Item 11.

A method for stabilizing an acrylic acid derivative represented by Formula (I):

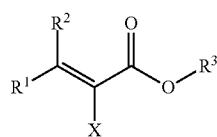

(I)

(wherein $R^1$ and $R^2$ are the same or different, and each represents alkyl, fluoroalkyl, aryl that may have one or more substituents, halogen, or hydrogen; $R^3$ represents alkyl, fluoroalkyl, aryl that may have one or more substituents, or hydrogen; and X represents fluoroalkyl, alkyl, halogen, or hydrogen), the method comprising making the acrylic acid derivative represented by Formula (I) coexist with alcohol.

Advantageous Effects of Invention

The composition of the present invention contains an acrylic acid derivative; in the composition, the acrylic acid derivative is stabilized.

The method of the present invention stabilizes an acrylic acid derivative.

DESCRIPTION OF EMBODIMENTS

Terms

The symbols and the abbreviations in this specification are to be interpreted as having the general meanings in the related technical field to which the present invention pertains, according to the context of this specification, unless otherwise specified.

In this specification, the term "comprise/contain" is intended to mean both "consist essentially of" and "consist of."

In this specification, "stabilization" of an acrylic acid derivative refers to preventing an acrylic acid derivative from changing into a different substance, such as a polymer.

In this specification, "alkyl" (the term "alkyl" encompasses the "alkyl" moiety in "fluoroalkyl" or the like) may be a cyclic, linear, or branched alkyl.

In this specification, "alkyl" may be, for example, a $C_{1-20}$, $C_{1-12}$, $C_{1-6}$, $C_{1-4}$, or $C_{1-3}$ alkyl.

In this specification, specific examples of "alkyl" include methyl, ethyl, propyl, isopropyl, butyl, isobutyl, sec-butyl, tert-butyl, pentyl, neopentyl, hexyl, and like linear or branched alkyl.

In this specification, specific examples of "alkyl" include cyclopropyl, cyclobutyl, cyclopentyl, cyclohexyl and like $C_{3-6}$ cyclic alkyl (cycloalkyl).

In this specification, "fluoroalkyl" refers to an alkyl in which at least one hydrogen is replaced by fluorine.

In this specification, the number of fluorines in the "fluoroalkyl" may be one or more (the maximum replaceable number from 1; e.g., 1 to 3, 1 to 6, or 1 to 12).

The "fluoroalkyl" encompasses perfluoroalkyl. The "perfluoroalkyl" refers to an alkyl in which all of the hydrogens are replaced by fluorines.

In this specification, examples of "fluoroalkyl" include $C_{1-20}$, $C_{1-12}$, $C_{1-6}$, $C_{1-4}$, and $C_{1-3}$ fluoroalkyls.

In this specification, the "fluoroalkyl" may be a linear or branched fluoroalkyl.

In this specification, specific examples of "fluoroalkyl" include fluoromethyl, difluoromethyl, trifluoromethyl, 2,2,2-trifluoroethyl, pentafluoroethyl, tetrafluoropropyl (e.g., $HCF_2CF_2CH_2-$), hexafluoropropyl (e.g., $(CF_3)_2CH-$), nonafluorobutyl, octafluoropentyl (e.g., $HCF_2CF_2CF_2CF_2CH_2-$), and tridecafluorohexyl.

In this specification, examples of "aryl" include phenyl and naphthyl.

In this specification, examples of "halogen" include fluorine, chlorine, bromine, and iodine.

In this specification, the "alkoxy" is an alkyl-O-group.

In this specification, examples of "acyl" include alkanoyl (i.e., alkyl-CO-group).

In this specification, examples of "ester" include alkylcarbonyloxy (i.e., alkyl-CO—O-group), and alkoxycarbonyl (i.e., alkyl-O—CO-group).

Composition

The composition of the present invention comprises:

(A) an acrylic acid derivative represented by Formula (I):

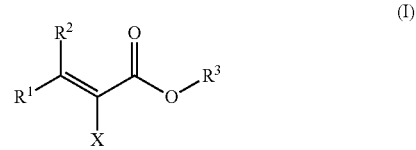

(I)

(wherein $R^1$ and $R^2$ are the same or different, and each represents alkyl, fluoroalkyl, aryl that may have one or more substituents, halogen, or hydrogen; $R^3$ represents alkyl, fluoroalkyl, aryl that may have one or more substituents, or hydrogen; and X represents fluoroalkyl, alkyl, halogen, or hydrogen]) (in this specification, this derivative may also be referred to as "acrylic acid derivative (A)"); and (B) alcohol, wherein the content of acrylic acid derivative (A) is 30% (w/w) or more.

Acrylic Acid Derivative (A)

Each symbol in Formula (1) representing acrylic acid derivative (A) is explained below.

Preferable examples of the substituents of the "aryl that may have one or more substituents" represented by $R^1$, $R^2$, and $R^3$ include fluorine, alkyl, alkoxy, acyl, ester, cyano, nitro, and fluoroalkyl. More preferable examples include fluorine.

The number of "the substituents" is preferably 0 (i.e., unsubstituted), 1, 2, or 3.

$R^1$ is preferably hydrogen, $C_{1-20}$ (preferably $C_{1-12}$, more preferably $C_{1-6}$, further preferably $C_{1-4}$, further more preferably $C_{1-3}$, particularly preferably $C_1$ or $C_2$) alkyl, or $C_{1-20}$ fluoroalkyl, and more preferably hydrogen.

$R^2$ is preferably hydrogen, $C_{1-20}$ (preferably $C_{1-12}$, more preferably $C_{1-6}$, further preferably $C_{1-4}$, further more preferably $C_{1-3}$, particularly preferably $C_1$ or $C_2$) alkyl, or $C_{1-20}$ (preferably $C_{1-12}$, more preferably $C_{1-6}$, further preferably $C_{1-4}$, further more preferably $C_{1-3}$, particularly preferably $C_1$ or $C_2$) fluoroalkyl, and more preferably hydrogen.

$R^3$ is preferably $C_{1-20}$ (preferably $C_{1-12}$, more preferably $C_{1-6}$, further preferably $C_{1-4}$, further more preferably $C_{1-3}$, particularly preferably $C_1$ or $C_2$) linear alkyl.

X is $C_{1-20}$ (preferably $C_{1-12}$, more preferably $C_{1-6}$, further preferably $C_{1-4}$, further more preferably $C_{1-3}$, particularly preferably $C_1$ or $C_2$) fluoroalkyl, fluorine, or chlorine, and more preferably fluorine.

In Formula (I), preferably,
$R^1$ is hydrogen,
$R^2$ is hydrogen,
$R^3$ is methyl or ethyl (more preferably methyl), and
X is fluorine or chlorine (more preferably fluorine).

The composition of the present invention may comprise one or more kinds of acrylic acid derivative (A); however, the composition of the present invention preferably comprises only one kind of acrylic acid derivative (A).

Acrylic acid derivative (A) used in the present invention may be produced by a known method or a similar method thereof, or may be obtained from commercial suppliers.

Acrylic acid derivative (A) used in the present invention may be produced, for example, through the production methods disclosed in International Publication No. 2014/034906, JP2014-24755A, U.S. Pat. No. 3,262,968, and the like, or similar methods thereof.

The content of acrylic acid derivative (A) in the composition of the present invention is 30% (w/w) or more.

Generally, when the concentration of acrylic acid derivative (A) is high, unintended polymerization reaction or the like more easily occurs. However, in the composition of the present invention, even when the content of acrylic acid derivative (A) is high, acrylic acid derivative (A) is stable.

Further, the content of acrylic acid derivative (A) in the composition of the present invention is preferably 35% (w/w) or more, 40% (w/w) or more, 50% (w/w) or more, 60% (w/w) or more, 70% (w/w) or more, 80% (w/w) or more, or 90% (w/w) or more.

Further, the content of acrylic acid derivative (A) in the composition of the present invention is preferably 30 to 90% (w/w), 30 to 80% (w/w), 35 to 70% (w/w), or 35 to 65% (w/w).

The upper limit of the content of acrylic acid derivative (A) in the composition of the present invention is, for example, but not particularly limited to, 98% (w/w), 95% (w/w), 90% (w/w), 80% (w/w), 70% (w/w), or 65% (w/w). However, as it would be obvious to a person skilled in the art, the upper limit of the content of acrylic acid derivative (A) in the composition of the present invention may be limited depending on the amount of alcohol (B) contained in the composition of the present invention.

Alcohol (B)

Alcohol (B) contained in the composition of the present invention is preferably $C_{1-6}$ alcohol.

Examples of alcohol (B) contained in the composition of the present invention include methanol, ethanol, n-propanol, isopropanol, n-butanol, isobutanol, tert-butanol, pentanol, and hexanol.

Alcohol (B) contained in the composition of the present invention is particularly preferably methanol.

In the present invention, alcohol (B) may be a single kind or a combination of two or more kinds of alcohol (B).

The lower limit of the content of alcohol (B) in the composition of the present invention is preferably 0.02% (w/w), more preferably 0.03% (w/w), further preferably 0.1% (w/w), further more preferably 0.3% (w/w), particularly preferably 0.5% (w/w), and particularly preferably 1% (w/w), 1.5% (w/w), 2.0% (w/w), particularly preferably 3.0%, more particularly preferably 5.0% (w/w).

In accomplishing the stabilization of acrylic acid derivative (A), in the composition of the present invention, the upper limit of the content of alcohol (B) is not particularly limited; however, using alcohol (B) in an amount more than the amount ensuring the desired stabilization of acrylic acid derivative (A) is a disadvantage in terms of cost. Therefore, the upper limit of the content of alcohol (B) in the composition of the present invention is generally, for example, 70% (w/w), 50% (w/w), 40% (w/w), 30% (w/w), 20% (w/w), 15% (w/w), 10% (w/w), 7% (w/w), 6% (w/w), 5% (w/w), 4% (w/w), or 3% (w/w).

The content of alcohol (B) in the composition of the present invention is preferably 0.01 to 70% (w/w), 0.01 to 50% (w/w), or in a range of 0.02 to 6% (w/w), more preferably in a range of 0.03 to 5% (w/w), further preferably in a range of 0.1 to 4% (w/w), further more preferably in a range of 0.3 to 3.5 (w/w), particularly preferably 0.5 to 3% (w/w), and further particularly preferably in a range of 1 to 3% (w/w).

In the composition of the present invention, the lower limit of the ratio of alcohol (B) to acrylic acid derivative (A) [alcohol (B)/acrylic acid derivative (A)] is preferably 0.02% (w/w), more preferably 0.03% (w/w), further preferably 0.1% (w/w), further more preferably 0.3% (w/w), particularly preferably 0.5% (w/w), and particularly preferably 1% (w/w).

In accomplishing the stabilization of acrylic acid derivative (A), the upper limit of the ratio of alcohol (B) to acrylic acid derivative (A) [alcohol (B)/acrylic acid derivative (A)] is not particularly limited; however, using alcohol (B) in an amount more than the amount ensuring the desired stabilization of acrylic acid derivative (A) is a disadvantage in terms of cost. Therefore, the upper limit of the ratio of alcohol (B) to acrylic acid derivative (A) [alcohol (B)/acrylic acid derivative (A)] is generally, for example, 200% (w/w), 190% (w/w), 170% (w/w), 150% (w/w), 100% (w/w), 70% (w/w), 50% (w/w), 40% (w/w), 30% (w/w), 20% (w/w), 15% (w/w), 10% (w/w), 7% (w/w), 6% (w/w), 5% (w/w), 4% (w/w), or 3% (w/w).

In the composition of the present invention, the ratio of alcohol (B) to acrylic acid derivative (A) is preferably 0.01 to 200% (w/w), 0.01 to 190% (w/w), 0.01 to 170% (w/w), 0.01 to 100% (w/w), or in a range of 0.02 to 6% (w/w), more preferably in a range of 0.03 to 5% (w/w), further preferably in a range of 0.1 to 4% (w/w), further more preferably in a range of 0.3 to 3.5 (w/w), particularly preferably 0.5 to 3% (w/w), and particularly preferably in a range of 1 to 3% (w/w).

Optional Components

The composition of the present invention may contain optional components in addition to acrylic acid derivative (A) and alcohol (B). The optional components may be impurities that coexist with acrylic acid derivative (A) or alcohol (B) prepared for the production of the composition of the present invention.

Examples of the optional components include water and organic solvents.

In the composition of the present invention, since acrylic acid derivative (A) is stabilized by alcohol (B), the significance of using a polymerization inhibitor for the purpose of stabilizing acrylic acid derivative (A) is small; however, the composition of the present invention may contain a polymerization inhibitor as an optional component.

As a method for preventing unintended polymerization reaction or the like, a method of using a polymerization inhibitor, such as the polymerization inhibitor disclosed in Patent Document 2, has been known. However, acrylic acid derivative (A) may be exposed to various conditions, for example, upon storage or at the time of use. Since the boiling points of versatile polymerization inhibitors greatly differ from that of an acrylic acid derivative, it is often difficult to make them coexist with an acrylic acid derivative. In this case, the polymerization inhibitors cannot fully exhibit its function.

Stability of the Composition of the Present Invention

In the composition of the present invention, acrylic acid derivative (A) is stabilized. More specifically, acrylic acid derivative (A) contained in the composition of the present invention has high stability.

Specifically, for example, acrylic acid derivative (A) in the composition of the present invention is prevented from changing into a polymer or the like, compared with a case in which acrylic acid derivative (A) does not coexist with alcohol (B).

In the present invention, the change of acrylic acid derivative (A) into a different substance may be analyzed, for example, using NMR analysis or the like. Further, for example, the change of acrylic acid derivative into a polymer may be easily detected by observation of a change of a colorless transparent solution of acrylic acid derivative into a solid, or the like.

In the composition of the present invention, acrylic acid derivative (A) is stabilized by the coexistence with alcohol (B).

A method for making the acrylic acid derivative coexist with a polymerization inhibitor has been known as a means for stabilizing an acrylic acid derivative.

However, since acrylic acid derivative (A) may be exposed to various conditions, for example, upon storage or at the time of use, the coexistence of a polymerization inhibitor with an acrylic acid derivative may be difficult in some cases. In this case, the polymerization inhibitor cannot fully exhibit its function.

In contrast, since alcohol (B) may have a boiling point similar to that of acrylic acid derivative (A), it is easy to make alcohol (B) coexist with acrylic acid derivative (A). Therefore, acrylic acid derivative (A) in the composition of the present invention is stable under various conditions.

In addition, when acrylic acid derivative (A) in the composition of the present invention is subjected to a polymerization reaction or the like, optionally, the reactivity of acrylic acid derivative (A) can be increased by removing alcohol (B) by a usual method such as washing with water.

Production Method

The composition of the present invention may be produced by mixing acrylic acid derivative (A), alcohol (B), and optional components using, for example, a usual method such as stirring.

Some or all of alcohol (B) may be contained as an impurity or an additive in acrylic acid derivative (A) prepared for the production of the composition of the present invention.

Method for Stabilizing Acrylic Acid Derivative (A)

The method for stabilizing the acrylic acid derivative (acrylic acid derivative (A)) represented by Formula (I) of the present invention comprises making acrylic acid derivative (A) coexist with alcohol (alcohol (B)).

The method for making acrylic acid derivative (A) coexist with alcohol (B) is not particularly limited. Examples of the method include:

[1] a method of mixing acrylic acid derivative (A) and alcohol (B);

[2] a method of producing alcohol (B) in a system containing acrylic acid derivative (A);

[3] a method of producing acrylic acid derivative (A) in a system containing alcohol (B); and

[4] a method of individually producing acrylic acid derivative (A) and alcohol (B) in a single system.

The same explanation of acrylic acid derivative (A) as that regarding the composition of the present invention can be applied to acrylic acid derivative (A) used in the method for stabilizing acrylic acid derivative (A) of the present invention.

The same explanation of alcohol (B) as that regarding the composition of the present invention can be applied to alcohol (B) used in the method for stabilizing acrylic acid derivative (A) of the present invention.

In the method for stabilizing acrylic acid derivative (A) of the present invention, preferably, alcohol (B) is used at a predetermined ratio relative to acrylic acid derivative (A). The ratio is as described above regarding the composition of the present invention.

The details of the method for stabilizing acrylic acid derivative (A) including the above matters can be understood from the above explanation regarding the composition of the present invention.

EXAMPLES

The present invention is described below in more detail with reference to Examples. However, the present invention is not limited to these Examples.

Compositions having the formulations shown in Table 1 were prepared. The compositions were colorless and transparent liquids.

Each composition was placed in a container, which was closed with a stopper. Stirring was performed for an hour at an outside temperature of 65° C., and generation of a solid was visually confirmed, thereby confirming whether a polymer was generated.

Generation of polymer was not confirmed in Composition a, b, c, d, or e.

In contrast, in Comparative Example 1 performed under the same conditions (methanol was not added), generation of polymer was confirmed.

Composition f was placed in a container, which was closed with a stopper. Stirring was performed for 30 minutes at an outside temperature of 40° C., and generation of a solid was visually confirmed, thereby confirming whether a polymer was generated.

Generation of polymer was not confirmed in composition f.

In contrast, in Comparative Example 2 performed under the same conditions (methanol was not added), generation of polymer was confirmed.

TABLE 1

| Composition | MeOH | 2-Fluoroacrylic Acid Methyl Ester |
| --- | --- | --- |
| a | 2.4% (w/w) | 97.6% (w/w) |
| b | 2.0% (w/w) | 98.0% (w/w) |
| c | 2.3% (w/w) | 97.7% (w/w) |
| d | 5.1% (w/w) | 94.9% (w/w) |
| e | 0.3% (w/w) | 99.7% (w/w) |
| Comparative Example 1 | Not added | 100% (w/w) |
| f | 0.02% (w/w) | 99.98% (w/w) |
| Comparative Example 2 | Not added | 100% (w/w) |

Example g 2-fluoroacrylic acid methyl ester purified by distillation as an acrylic acid derivative and methyl alcohol at a weight ratio of 35:65 were placed in a 10-mL test tube. The test tube was closed with a stopper and mixing was performed, thereby preparing a sample. Regarding the appearance and the characteristics of the composition sample immediately after the preparation, the composition sample was a colorless and transparent liquid.

The test tube containing the sample was allowed to stand at 40° C., and the appearance and the characteristics of the sample were confirmed after six hours; the composition sample was a colorless and transparent liquid.

Example h 2-fluoroacrylic acid methyl ester purified by distillation as an acrylic acid derivative and methyl alcohol at a weight ratio of 60:40 were placed in a 10-mL test tube. The test tube was closed with a stopper and mixing was performed, thereby preparing a sample. Regarding the appearance and the characteristics of the composition sample immediately after the preparation, the composition sample was a colorless and transparent liquid.

The test tube containing the sample was allowed to stand at 40° C., and the appearance and the characteristics of the sample were confirmed after six hours; the composition sample was a colorless and transparent liquid.

Example i 2-fluoroacrylic acid methyl ester purified by distillation as an acrylic acid derivative and methyl alcohol at a weight ratio of 35:65 were placed in a 10-mL test tube. The test tube was closed with a stopper and mixing was performed, thereby preparing a sample. Regarding the appearance and the characteristics of the composition sample immediately after the preparation, the composition sample was a colorless and transparent liquid.

The test tube containing the sample was allowed to stand at 65° C., and the appearance and the characteristics of the sample were confirmed after six hours; the composition sample was a colorless and transparent liquid.

Example j 2-fluoroacrylic acid methyl ester purified by distillation as an acrylic acid derivative and methyl alcohol at a weight ratio of 60:40 were placed in a 10 mL test tube. The test tube was closed with a stopper and mixing was performed, thereby preparing a sample. Regarding the appearance and the characteristics of the composition sample immediately after the preparation, the composition sample was a colorless and transparent liquid.

The test tube containing the sample was allowed to stand at 65° C., and the appearance and the characteristics of the sample were confirmed after six hours; the composition sample was a colorless and transparent liquid.

The invention claimed is:

1. A composition comprising:
(A) an acrylic acid derivative represented by Formula (I):

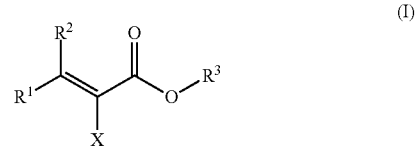

wherein $R^1$ and $R^2$ are the same or different, and each represents alkyl, fluoroalkyl, aryl that may have one or more substituents, halogen, or hydrogen; $R^3$ represents alkyl, fluoroalkyl, aryl that may have one or more substituents, or hydrogen; and X is $C_{1-20}$ fluoroalkyl, fluorine, or chlorine; and
(B) alcohol,
wherein the content of acrylic acid derivative (A) is 30% (w/w) or more.

2. The composition according to claim 1, wherein alcohol (B) is $C_{1-6}$ alcohol.

3. The composition according to claim 2, wherein alcohol (B) is methanol.

4. The composition according to claim 1, wherein $R^1$ is hydrogen, $C_{1-20}$ alkyl, or $C_{1-20}$ fluoroalkyl.

5. The composition according to claim 1, wherein $R^1$ is hydrogen.

6. The composition according to claim 1, wherein $R^2$ is hydrogen, $C_{1-20}$ alkyl, or $C_{1-20}$ fluoroalkyl.

7. The composition according to claim 1, wherein $R^2$ is hydrogen.

8. The composition according to claim 1, wherein $R^3$ is $C_{1-20}$ linear alkyl.

9. The composition according to claim 1, wherein X is fluorine.

10. A method for stabilizing (A) an acrylic acid derivative represented by Formula (I):

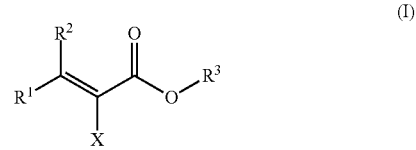

wherein $R^1$ and $R^2$ are the same or different, and each represents alkyl, fluoroalkyl, aryl that may have one or more substituents, halogen, or hydrogen; $R^3$ represents alkyl, fluoroalkyl, aryl that may have one or more substituents, or hydrogen; and X represents fluoroalkyl, alkyl, halogen, or hydrogen,
the method comprising making the acrylic acid derivative represented by Formula (I) coexist with alcohol.

* * * * *